United States Patent
Cohen et al.

(10) Patent No.: US 7,485,453 B2
(45) Date of Patent: Feb. 3, 2009

(54) DIFFRACTION-BASED DIAGNOSTIC DEVICES

(75) Inventors: David Cohen, Alpharetta, GA (US); Rosann Kaylor, Cumming, GA (US)

(73) Assignee: Kimberly-Clark Worldwide, Inc.

( * ) Notice: Subject to any disclaimer, the term of this patent is extended or adjusted under 35 U.S.C. 154(b) by 418 days.

(21) Appl. No.: 10/139,018

(22) Filed: May 3, 2002

(65) Prior Publication Data

US 2003/0207257 A1 Nov. 6, 2003

(51) Int. Cl.
*C12M 1/34* (2006.01)

(52) U.S. Cl. .............. 435/287.1; 435/283.1; 435/287.2; 435/288.3; 435/7.1; 422/50; 422/61; 422/68.1; 422/82.11

(58) Field of Classification Search .............. 435/283.1, 435/287.1, 287.2, 288.3, 4, 7.1; 422/50, 422/61, 68.1, 82.11; 356/300, 302, 305; 436/518, 524, 525

See application file for complete search history.

(56) References Cited

U.S. PATENT DOCUMENTS

| | | |
|---|---|---|
| 3,641,354 A | 2/1972 | De Ment |
| 4,011,009 A | 3/1977 | Lama et al. |
| 4,274,706 A | 6/1981 | Tangonan |
| 4,312,228 A | 1/1982 | Wohltjen |
| 4,330,175 A | 5/1982 | Fujii et al. |
| 4,363,874 A | 12/1982 | Greenquist |
| 4,399,686 A | 8/1983 | Kindlund et al. |
| 4,416,505 A | 11/1983 | Dickson |
| 4,442,204 A | 4/1984 | Greenquist et al. |
| 4,477,158 A | 10/1984 | Pollock et al. |
| 4,480,042 A | 10/1984 | Craig et al. |
| 4,528,260 A | 7/1985 | Kane |
| 4,534,356 A | 8/1985 | Papadakis |
| 4,537,861 A | 8/1985 | Elings et al. |
| 4,552,458 A | 11/1985 | Lowne |
| 4,561,286 A | 12/1985 | Sekler et al. |
| 4,562,157 A | 12/1985 | Lowe et al. |
| 4,587,213 A | 5/1986 | Malecki |
| 4,596,697 A | 6/1986 | Ballato |
| 4,614,723 A | 9/1986 | Schmidt et al. |
| 4,632,559 A | 12/1986 | Brunsting |
| 4,647,544 A | 3/1987 | Nicoli et al. |
| 4,661,235 A | 4/1987 | Krull et al. |
| 4,690,715 A | 9/1987 | Allara et al. |

(Continued)

FOREIGN PATENT DOCUMENTS

EP 0205698 A1 12/1986

(Continued)

OTHER PUBLICATIONS

Bamdad, A DNA Self-Assembled Monolayer for the Specific Attachment of Unmodified Double- or Single-Stranded DNA, 1998, Biophysical Journal, vol. 75, pp. 1997-2003.*

(Continued)

*Primary Examiner*—Long V Le
*Assistant Examiner*—Melanie J. Yu
(74) *Attorney, Agent, or Firm*—Dority & Manning, P.A.

(57) ABSTRACT

A biosensor includes a substrate with areas of active receptive material disposed thereon. The receptive material is specific for an analyte of interest. A pattern of the active areas is defined on the substrate by an oxidizing photo-masking process.

19 Claims, 2 Drawing Sheets

U.S. PATENT DOCUMENTS

| | | | |
|---|---|---|---|
| 4,698,262 A | 10/1987 | Schwartz et al. | |
| 4,776,944 A | 10/1988 | Janata et al. | |
| 4,812,221 A | 3/1989 | Madou et al. | |
| 4,815,843 A | 3/1989 | Tiefenthaler et al. | |
| 4,818,710 A | 4/1989 | Sutherland et al. | |
| 4,837,715 A | 6/1989 | Ungpiyakul et al. | |
| 4,842,633 A | 6/1989 | Kuribayashi et al. | |
| 4,842,783 A | 6/1989 | Blaylock | |
| 4,844,613 A | 7/1989 | Batchelder et al. | |
| 4,851,816 A | 7/1989 | Macias et al. | |
| 4,876,208 A | 10/1989 | Gustafson et al. | |
| 4,877,747 A | 10/1989 | Stewart | |
| 4,882,288 A | 11/1989 | North et al. | |
| 4,895,017 A | 1/1990 | Pyke et al. | |
| 4,917,503 A | 4/1990 | Bhattacharjee | |
| 4,931,384 A | 6/1990 | Layton et al. | |
| 4,992,385 A | 2/1991 | Godfrey | |
| 4,999,489 A | 3/1991 | Huggins | |
| RE33,581 E | 4/1991 | Nicoli et al. | |
| 5,023,053 A | 6/1991 | Finlan | |
| 5,035,863 A | 7/1991 | Finlan et al. | |
| 5,055,265 A | 10/1991 | Finlan | |
| 5,057,560 A | 10/1991 | Mueller | |
| 5,063,081 A | 11/1991 | Cozzette et al. | |
| 5,064,619 A | 11/1991 | Finlan | |
| 5,071,248 A | 12/1991 | Tiefenthaler et al. | |
| 5,076,094 A | 12/1991 | Frye et al. | |
| 5,089,387 A | 2/1992 | Tsay et al. | |
| 5,096,671 A | 3/1992 | Kane et al. | |
| 5,114,676 A | 5/1992 | Leiner et al. | |
| 5,124,254 A | 6/1992 | Hewlins et al. | |
| 5,134,057 A | 7/1992 | Kuypers et al. | |
| 5,137,609 A | 8/1992 | Manian et al. | |
| 5,143,854 A | 9/1992 | Pirrung et al. | |
| 5,152,758 A | 10/1992 | Kaetsu et al. | |
| 5,155,791 A | 10/1992 | Hsiung | |
| 5,182,135 A | 1/1993 | Giesecke et al. | |
| 5,189,902 A | 3/1993 | Groeninger | |
| 5,196,350 A | 3/1993 | Backman et al. | |
| 5,225,935 A | 7/1993 | Watanabe et al. | |
| 5,235,238 A | 8/1993 | Nomura et al. | |
| 5,238,815 A | 8/1993 | Higo et al. | |
| 5,242,828 A | 9/1993 | Bergstrom et al. | |
| 5,262,299 A | 11/1993 | Evangelista et al. | |
| 5,268,306 A | 12/1993 | Berger et al. | |
| 5,280,548 A | 1/1994 | Atwater et al. | |
| 5,304,293 A | 4/1994 | Tierney et al. | |
| 5,310,686 A | 5/1994 | Sawyers et al. | |
| 5,315,436 A | 5/1994 | Lowenhar et al. | |
| 5,321,492 A | 6/1994 | Detwiler et al. | |
| 5,327,225 A | 7/1994 | Bender et al. | |
| 5,334,303 A | 8/1994 | Muramatsu et al. | |
| 5,352,582 A | 10/1994 | Lichtenwalter et al. | |
| 5,369,717 A | 11/1994 | Attridge | |
| 5,374,563 A | 12/1994 | Maule | |
| 5,376,255 A | 12/1994 | Gumbrecht et al. | |
| 5,378,638 A | 1/1995 | Deeg et al. | |
| 5,389,534 A | 2/1995 | von Gentzkow et al. | |
| 5,402,075 A | 3/1995 | Lu et al. | |
| 5,404,756 A | 4/1995 | Briggs et al. | |
| 5,415,842 A | 5/1995 | Maule | |
| 5,418,136 A | 5/1995 | Miller et al. | |
| 5,424,220 A | 6/1995 | Goerlach-Graw et al. | |
| 5,430,815 A | 7/1995 | Shen et al. | |
| 5,436,161 A | 7/1995 | Bergstrom et al. | |
| 5,451,683 A | 9/1995 | Barrett et al. | |
| 5,455,178 A | 10/1995 | Fattinger | |
| 5,455,475 A | 10/1995 | Josse et al. | |
| 5,464,741 A | 11/1995 | Hendrix | |
| 5,468,606 A | 11/1995 | Bogart et al. | |
| 5,478,527 A | 12/1995 | Gustafson et al. | |
| 5,482,830 A | 1/1996 | Bogart et al. | |
| 5,482,867 A | 1/1996 | Barrett et al. | |
| 5,489,678 A | 2/1996 | Fodor et al. | |
| 5,489,988 A | 2/1996 | Ackley et al. | |
| 5,492,840 A | 2/1996 | Malmqvist et al. | |
| 5,496,701 A | 3/1996 | Pollard-Knight | |
| 5,510,481 A | 4/1996 | Bednarski et al. | |
| 5,510,628 A * | 4/1996 | Georger et al. | 257/32 |
| 5,512,131 A | 4/1996 | Kumar et al. | |
| 5,514,501 A | 5/1996 | Tarlov | |
| 5,514,559 A | 5/1996 | Markert-Hahn et al. | |
| 5,516,635 A | 5/1996 | Ekins et al. | |
| 5,518,689 A | 5/1996 | Dosmann et al. | |
| 5,527,711 A | 6/1996 | Tom-Moy et al. | |
| 5,552,272 A | 9/1996 | Bogart | |
| 5,554,541 A | 9/1996 | Malmqvist et al. | |
| 5,569,608 A | 10/1996 | Sommer | |
| 5,573,909 A | 11/1996 | Singer et al. | |
| 5,580,697 A | 12/1996 | Keana et al. | |
| 5,580,921 A | 12/1996 | Stepp et al. | |
| 5,585,279 A | 12/1996 | Davidson | |
| 5,589,401 A | 12/1996 | Hansen et al. | |
| 5,591,581 A | 1/1997 | Massey et al. | |
| 5,599,668 A | 2/1997 | Stimpson et al. | |
| 5,620,850 A | 4/1997 | Bamdad et al. | |
| 5,637,509 A | 6/1997 | Hemmila et al. | |
| 5,643,681 A | 7/1997 | Voorhees et al. | |
| 5,658,443 A | 8/1997 | Yamamoto et al. | |
| 5,677,196 A * | 10/1997 | Herron et al. | 436/518 |
| 5,731,147 A | 3/1998 | Bard et al. | |
| 5,780,251 A | 7/1998 | Klainer et al. | |
| 5,811,526 A | 9/1998 | Davidson | |
| 5,814,565 A | 9/1998 | Reichert et al. | |
| 5,827,748 A | 10/1998 | Golden | |
| 5,830,762 A | 11/1998 | Weindel | |
| 5,832,165 A | 11/1998 | Reichert et al. | |
| 5,843,692 A | 12/1998 | Phillips et al. | |
| 5,863,740 A | 1/1999 | Kientsch-Engel et al. | |
| 5,910,940 A | 6/1999 | Guerra | |
| 5,922,537 A | 7/1999 | Ewart et al. | |
| 5,922,550 A | 7/1999 | Everhart et al. | |
| 5,922,615 A | 7/1999 | Nowakowski et al. | |
| 5,965,305 A | 10/1999 | Ligler et al. | |
| 6,030,840 A | 2/2000 | Mullinax et al. | |
| 6,048,623 A | 4/2000 | Everhart et al. | |
| 6,060,237 A | 5/2000 | Nygren et al. | |
| 6,060,256 A | 5/2000 | Everhart et al. | |
| 6,084,683 A | 7/2000 | Bruno et al. | |
| 6,107,038 A | 8/2000 | Choudhary et al. | |
| 6,113,855 A | 9/2000 | Buechler | |
| 6,136,611 A | 10/2000 | Saaski et al. | |
| 6,171,780 B1 | 1/2001 | Pham et al. | |
| 6,180,288 B1 | 1/2001 | Everhart et al. | |
| 6,182,571 B1 | 2/2001 | Jolliffe et al. | |
| 6,200,820 B1 | 3/2001 | Hansen et al. | |
| 6,203,758 B1 * | 3/2001 | Marks et al. | 422/68.1 |
| 6,221,579 B1 | 4/2001 | Everhart et al. | |
| 6,287,783 B1 | 9/2001 | Maynard et al. | |
| 6,287,871 B1 | 9/2001 | Herron et al. | |
| 6,297,060 B1 | 10/2001 | Nowakowski et al. | |
| 6,312,961 B1 | 11/2001 | Voirin et al. | |
| 6,331,438 B1 | 12/2001 | Aylott et al. | |
| 6,362,011 B1 | 3/2002 | Massey et al. | |
| 6,395,558 B1 | 5/2002 | Duveneck et al. | |
| 6,399,295 B1 | 6/2002 | Kaylor et al. | |
| 6,399,397 B1 | 6/2002 | Zarling et al. | |
| 6,411,439 B2 | 6/2002 | Nishikawa | |
| 6,416,952 B1 * | 7/2002 | Pirrung et al. | 435/6 |
| 6,423,465 B1 | 7/2002 | Hawker et al. | |
| 6,436,651 B1 | 8/2002 | Everhart et al. | |
| 6,448,091 B1 | 9/2002 | Massey et al. | |
| 6,455,861 B1 | 9/2002 | Hoyt | |
| 6,468,741 B1 | 10/2002 | Massey et al. | |

| | | | |
|---|---|---|---|
| 6,556,299 B1 | 4/2003 | Rushbrooke et al. | |
| 6,573,040 B2 | 6/2003 | Everhart et al. | |
| 6,579,673 B2 | 6/2003 | McGrath et al. | |
| 6,582,930 B1 | 6/2003 | Ponomarev et al. | |
| 6,613,583 B1 | 9/2003 | Richter et al. | |
| 6,653,151 B2 | 11/2003 | Anderson et al. | |
| 6,743,581 B1 | 6/2004 | Vo-Dinh | |
| 6,790,531 B2 | 9/2004 | Fournier | |
| 7,256,054 B2 * | 8/2007 | Sluka et al. | 436/525 |
| 2002/0025534 A1 * | 2/2002 | Goh et al. | 435/7.1 |
| 2002/0028455 A1 | 3/2002 | Laibinis et al. | |
| 2003/0027327 A1 | 2/2003 | Cunningham et al. | |
| 2003/0207253 A1 | 11/2003 | Kaylor et al. | |
| 2003/0207254 A1 | 11/2003 | Cohen et al. | |
| 2003/0207255 A1 | 11/2003 | Cohen et al. | |
| 2003/0207256 A1 | 11/2003 | Sayre et al. | |
| 2003/0207258 A1 | 11/2003 | Cohen et al. | |
| 2004/0002110 A1 | 1/2004 | Boga et al. | |
| 2004/0058385 A1 | 3/2004 | Abel et al. | |
| 2004/0063146 A1 | 4/2004 | Sayre et al. | |

FOREIGN PATENT DOCUMENTS

| | | | |
|---|---|---|---|
| EP | 0420053 A1 | 4/1991 | |
| EP | 0453820 A2 | 10/1991 | |
| EP | 0453820 A3 | 10/1991 | |
| EP | 0453820 B1 | 10/1991 | |
| EP | 0539035 A2 | 4/1993 | |
| EP | 0539035 B1 | 4/1993 | |
| EP | 0596421 A1 | 5/1994 | |
| EP | 0657737 A2 | 6/1995 | |
| EP | 0657737 A3 | 6/1995 | |
| EP | 1566627 A1 | 8/2005 | |
| GB | 2273772 | 6/1994 | |
| WO | 9005305 | 5/1990 | |
| WO | 9105999 | 5/1991 | |
| WO | 9113998 A1 | 9/1991 | |
| WO | 9403496 | 2/1994 | |
| WO | WO 9413835 A1 | 6/1994 | |
| WO | 9415193 | 7/1994 | |
| WO | WO 9609532 A1 | 3/1996 | |
| WO | 9615193 | 5/1996 | |
| WO | WO 9612962 A1 | 5/1996 | |
| WO | 9626435 | 8/1996 | |
| WO | WO 9624062 A1 | 8/1996 | |
| WO | 9629629 | 9/1996 | |
| WO | 9633971 | 10/1996 | |
| WO | WO 9301308 A1 | 1/1998 | |
| WO | 9810334 | 3/1998 | |
| WO | WO 9815831 A1 | 4/1998 | |
| WO | 9827417 | 6/1998 | |
| WO | WO 9910742 A1 | 3/1999 | |
| WO | WO 9930131 A1 | 6/1999 | |
| WO | WO 9931486 A1 | 6/1999 | |
| WO | WO 0050891 A1 | 8/2000 | |
| WO | WO 0171322 A2 | 9/2001 | |
| WO | WO 0181921 A2 | 11/2001 | |
| WO | WO 0181921 A3 | 11/2001 | |

OTHER PUBLICATIONS

Optical Biosensor Assay (OBA), Clin. Chem. 37/9, 1502-1505 (1991), vol. 37, No. 9.
Article—*Chromophore-assisted laser inactivation of proteins is mediated by the photogeneration of free radicals,* Joseph C. Liao, Johann Roider, and Daniel G. Jay, Proc. Natl. Acad. Sci. USA, vol. 91, Mar. 1994, pp. 2659-2663.
Article—*Laser-Mediated Protein Inactivation for Target Validation,* Jens Niewöhner, Susanne Rubenwolf, Elisabeth Meyer, and Fritz Rudert, Jul./Aug. 2001, pp. 28-33.
PCT Search Report for PCT/US03/29005, Feb. 12, 2004.
PCT Search Report for PCT/US03/11757, May 4, 2004.
PCT Search Report for PCT/US03/11757, May 6, 2004.
Abstract of Japanese Patent No. JP2085755, Mar. 27, 1990.
Abstract of Japanese Patent No. JP2140702, May 20, 1990.
Abstract of Japanese Patent No. JP2165933, Jun. 26, 1990.
Abstract of Japanese Patent No. JP2210302, Aug. 21, 1990.
Abstract of Japanese Patent No. JP5132640, May 28, 1993.
Abstract of Japanese Patent No. JP8062214, Mar. 8, 1996.
Article—*A New Tetradentate β-Diketonate-Europium Chelate That Can Be Covalently Bound to Proteins for Time-Resolved Fluoroimmunoassay,* Jingli Yuan and Kazuko Matsumoto, Analytical Chemistry, vol. 70, No. 3, Feb. 1, 1998, pp. 596-601.
Article—*Europium Chelate Labels in Time-Resolved Fluorescence Immunoassays and DNA Hybridization Assays,* Eleftherios P. Diamandis and Theodore K. Christopoulos, Analytical Chemistry, vol. 62, No. 22, Nov. 15, 1990, pp. 1149-1157.
Article—*Evaluation of a Time-Resolved Fluorescence Microscope Using a Phosphorescent Pt-Porphine Model System,* E. J. Hennink, R. de Haas, N. P. Verwoerd, and H. J. Tanke, Cytometry, vol. 24, 1996, pp. 312-320.
Article—*Immunoaffinity Based Phosphorescent Sensor Platform for the Detection of Bacterial Spores,* Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Article—*Inert Phorphorescent Nanaspheres as Markers for Optical Assays,* Jens M. Kümer, Ingo Klimant, Christian Krause, Harald Preu, Werner Kunz, and Otto S. Wolfbeis, Bioconjugate Chem., vol. 12, 2001, pp. 883-889.
Article—*Latex Immunoassays,* Leigh B. Bangs, Journal of Clinical Immunoassay, vol. 13, No. 3, 1990, pp. 127-131.
Article—*Longwave luminescent porphyrin probes,* Dmitry B. Papkovsky, Gelii V. Ponomarev, and Otto S. Wolfbeis, Spectrochimica Acta Part A, vol. 52, 1996, pp. 1629-1638.
Article—*Monofunctional Derivatives of Coproporphyrins for Phosphorescent Labeling of Proteins and Binding Assays,* Analytical Biochemistry, vol. 290, 2001, pp. 366-375.
Article—*Near Infrared Phosphorescent Metalloporphyrins,* Alexander P. Savitsky, Anna V. Savitskaja, Eugeny A. Lukjanetz, Svetlana N. Dashkevich, and Elena A. Makarova, SPIE, vol. 2980, pp. 352-357.
Article—*One-step all-in-one dry reagent immunoassays with fluorescent europium chelate label and time-resolved fluorometry,* Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.
Article—*Performance Evaluation of the Phosphorescent Porphyrin Label: Solid-Phase Immunoassay of α-Fetoprotein,* Tomás C. O'Riordan, Aleksi E. Soini, Juhani T. Soini, and Dmitri B. Papkovsky, Analytical Chemistry, Vo. 74, No. 22, Nov. 15, 2002, pp. 5845-5850.
Article—*Phosphorescent porphyrin probes in biosensors and sensitive bioassays,* D. B. Papkovsky, T. O'Riordan, and A. Soini, Biochemical Society Transactions, vol. 28, Part 2, 2000, pp. 74-77.
Article—*Polymer Based Lanthanide Luminescent Sensors for the Detection of Nerve Agents,* Amanda L. Jenkins, O. Manuel Uy, and George M. Murray, Analytical Communications, vol. 34, Aug. 1997, pp. 221-224.
Article—*Room-Temperature Phosphorescent Palladium—Porphine Probe for DNA Dtermination,* Montserrat Roza-Fernández, Maria Jesús Valencia-González, and Marta Elena Diaz-Garcia, Analytical Chemistry, vol. 69, No. 13, Jul. 1, 1997, pp. 2406-2410.
*FluoSpheres® Fluorescent Microspheres,* Product Information from Molecular Probes, Mar. 13, 2001, pp. 1-6.
*Working With FluoSpheres® Fluorescent Microspheres,* Properties and Modifications, Product Information from Molecular Probes, Mar. 9, 2001, pp. 1-5.
Letter to the Editors, Comment on the Prediction of Segregation to Alloy Surfaces, copyright-1977, p. 200-202.
Prediction of Segregation to Alloy Surfaces From Bulk Phase Diagrams, Physical Review Letters, vol. 37, No. 21, Nov. 22, 1976, p. 1433-1435.
Orientation Dependence of Surface Segregation in a Dilute Ni-Au Alloy, Research Staff, Ford Motor Company, Dearborn, MI, Received Sep. 19, 1977; Accepted Nov. 18, 1977, p. 467-469.

Volume Phase Transition of N-Alkylacrylamide Gels, Department of Molecular Chemistry and Engineering, Tohoku University, Advances on Polymer Science, vol. 109, 1993, p. 207-232.

Molecular Gradients of w-Substituted Alkanethiols on Gold: Preparation and Characterization, Laboratory of Applied Physics, 1995 American Chemical Society, Jun. 6, 1995, p. 3821-3827.

Acoustic Plate Waves for Measurements of Electrical Properties of Liquids, Microchemical Journal 43, p. 155-164, Jan. 31, 1991.

Analysis of Electrical Equivalent Circuit of Quartz Crystal Resonator Loaded With Viscous Conductive Liquids, Journal of Electroanalytical Chemistry 379 (1994)p. 21-33, Apr. 12, 1994.

Quartz Crystal Resonators as Sensors in Liquids Using the Acoustoelectric Effect, Anal. Chem. 1994, 66, p. 1955-1964.

Features of Gold Having Micrometer to Centimeter Dimensions can be Formed Through a Combination of Stamping With an Elastomeric Stamp and an Alkanethiol "Ink" Following by Chemical Etching, Appl. Phys. Lett. 63 (14), Oct. 4, 1993, p. 2002-2004.

Photolithography of Self-Assembled Monolayers: Optimization of Protecting Roups by an Electroanalytical Method, Can. J. Chem 74; p. 2509-2517 (1996).

Order in Microcontact Printed Self-Assembled Monolayers, Contributions of the IBM Research Division, Nov. 26, 1996, p. 3017-3026.

Combining Patterned Self-Assembled Monolayers of Alkanethiolates on Gold With Anisotropic Etching of Silicon to Generate Controlled Surface Morphologies, J. Electrochem. Soc., vol. 142, No. 2, Feb. 1995, p. 628-633.

109 Advances in Polymer Science, Responsive Gels: Volume Transitions I, Springer Verlag Berlin Heidelberg 1993, p. 1-5.

110 Advances in Polymer Science, Responsive Gels: Volume Transitions II, Springer Verlag Berlin Heidelberg 1993, p. 1-269.

Intelligent Gels, Scientific American May 1993, p. 82-87.

Volume Phase Transition and Related Phenomena of Polymer Gels, Advances in Polymer Science, vol. 109, Springer-Verlag Berlin Heidelberg 1993, p. 1-62.

Novel Applications for Stimulus-Sensitive Polymer Gels in the Preparation of Functional Immobilized Biocatalysts, Advances in Polymer Science, vol. 110, Verlag Berlin Heidelberg 1993, p. 157-177.

Stimuli-Responsive Polymer Gels and Their Application to Chemomechanical Systems, Prg. Polym. Sci. vol. 18, p. 187-226, 1993.

Electrical Surface Perturbation of a Piezoelectric Acoustic Plate Mode by a Conductive Liquid Loading, IEEE Transactions on Ulstrasonics, Ferroelectrics, and Frequency Control, vol. 39, No. 4, Jul. 1992, p. 512-518.

On the use of ZX-LiNbO$_3$ Acoustic Plate Mode Devices as Detectors for Dilute Electrolytes, Sensors and Actuators B.9 (1992) p. 97-112.

Probing of Strong and Weak Electrolytes With Acoustic Wave Fields, Sensors and Actuators B. 9 (1992) p. 155-162.

Using Micromachining, Molecular Self-Assembly, and Wet Etching to Fabricate 0.1-1 um Scale Structures of Gold and Silicon, Chemistry of Materials, 1994, p. 596-602.

Patterned Self-Assembled Monolayers Formed by Microcontact Printing Direct Selective Metalization by Chemical Vapor Deposition on Planar and Nonplanar Substrates, Langmuir 1995, 11, p. 3024-3026.

Self-Assembled Monolayers of Long-Chain Hydroxamic Acis on the Native Oxides of Metals, Langmuir, 1995, 11 p. 813-824.

Microfabrication by Microcontact Printing of Self-Assembled Monolayers, VCH Verlagsgesellschaf T mbH, 1994 p. 600-604.

Patterned Condensation Figures as Optical Diffraction Gratings, American Association for the Advancement of Science, 1994, p. 60-62.

Stimuli-Responsive Pol. (N-Isoproplylacrylamide). Photo- and Chemical-Induced Phase Transitions, Advances in Polymer Science No. 110, 1993, p. 50-65.

Quantitative Prediction of Surface Segregation, Journal of Catalysis 57, p. 450-457 (1970).

Sensing Liquid Properties With Thickness-Shear Mode Reasonators, Sensors and Actuators A 44 (1944) 209-218.

Direct Observation of Streptavidin Specifically Adsorbed on Biotin-Functionalized Self-Assembled Monolayers With the Scanning Tunneling Microscope, Angew Chem. Int. Ed. Engl. 30 (1991) No. 5 p. 569-572.

New Approach to Producing Patterned Biomolecular Assemblies, Journal of the American Chemical Society, 1992, p. 4432-4433.

The Biotin-(Strept) Avidin System: Principles and Applications in Biotechnology, Clinical Chemistry, vol. 37, No. 5, 1991, p. 625-636.

Fabrication of Surfaces Resistant to Protein Adsorption and Application to Two-Dimensional Protein Patterning, Analytical Biochemistry 208, p. 197-205 (1993).

Photosensitive Self-Assembled Monolayers on Gold: Photochemistry of Surface-Confined Aryl Azide and Cyclopentadienylmanganese Tricarbonyl, American Chemical Society, 1994, p. 4395-4401.

Generation of Electrochemically Deposited Metal Patterns by Means of Electron Beam (Nano)Lithography of Self-Assembled Monolayer Resists, American Institute of Physics, 1994, p. 205-207.

Selective Electrochemical Deposition of Polyaniline Via Photopatterning of a Monolayer-Modified Substrate, American Chemical Society 1994, p. 5993-5994.

Pattern Transfer of Electron Beam Modified Self-Assembled Monolayers for High-Resolution Lithography, J. Vac. Sci. Technol. B 13(3) May/Jun. 1995, p. 1139-1143.

Patterned Functionalization of Gold and Single Crystal Silicon Via Photochemical Reaction of Surface-Confined Derivatives of ($N^5$-$C_5H_5$)Mn(CO)$_3$, American Chemical Society 1991, p. 2169-2174.

Control of the Shape of Liquid Lenses on a Modified Gold Surface Using an Applied Electrical Potential Across a Self-Assembled Monolayer, American Chemical Society 1995, p. 2242-2246.

Wet Chemical Approaches to the Characterization of Organic Surfaces: Self-Assembled Monolyers, Wetting, and the Physical-Organic Chemistry of the Solid-Liquid Interface, Department of Chemistry, Harvard University, 1989, p. 87-96.

UV Photpatterning of Alkanethiolate Monolayers Self-Assembled on Gold and Silver, American Chemical Society 1993, p. 5305-5306.

The Use of Self-Assembled Monolayers and a Selective Etch to Generate Patterned Gold Features, American Chemical Society 1992, p. 9188-9189.

Use of Patterned Self-Assembled Monolayer to Control the Formation of a Liquid Resist Pattern on a Gold Surface, American Chemical Society 1995, p. 252-254.

Self-Organization of Organic Liquids on Patterned Self-Assembled Monolayers of Alkanethiolates on Gold, Langmuir 1994, p. 2790-2793.

Self-Assembled Monolayer Electron Beam Resist on GaAS, American Institute of Physics 1993, p. 475-479.

Manipulation of the Wettability of Surfaces on the 0.1-to 1-Micrometer Scale Through Micromachining and Molecular Self-Assembly, Science, vol. 257, Sep. 1992, p. 1380-1382.

Comparison of the Structures and Wetting Properties of Self-Assembled Monolayers of n-Alkanethiols on the Coinage Metal Surfaces, Cu, Ag, Au, American Chemical Society, 1991, p. 7152-7167.

Self-Assembled Monolayer Films for Nanofabrication, Mat. Res. Soc. Symp. Proc. vol. 380, 1995 Materials Research Society, p. 23-34.

Patterned Metal Electrodeposition Using an Alkanethiolate Mask, J. Electrochem. Soc. vol. 142, No. 11, Nov. 1995, p. L220-L222.

Biospecific Adsorption of Carbonic Anhydrase to Self-Assembled Monolayers of Alkanethiolates That Present Benzenesulfonamide Groups on Gold, American Chemical Society, 1995, p. 12009-12010.

Attempts to Mimic Docking Processes of the Immune System: Recognition-Induced Formation of Protein Multilayers, Science, vol. 262, Dec. 10, 1993, p. 1706-1708.

Mechanical Resonance Gas Sensors With Piezoelectric Excitation and Detection Using PVDF Polymer Foils, Elsevier Sequoia 1992 p. 596-601.

Application of Rod-Like Polymers With Ionophores as Langmuir-Blodgett Membrances for Si-Based Ion Sensors, Elsevier Sequoia 1992, p. 211-216.

Patterning Self-Assembled Monolayers: Applications in Materials Science, Department of Chemistry, Harvard University, Feb. 18, 1994, p. 1498-1511.

Article—*A Fill-and-Flow Biosensor,* Gooding et al, Analytical Chemistry, vol. 70, No. 15, Aug. 1, 1999, pp. 3131-3136.

Article—*Diffraction-Based Cell Detection Using a Microcontact Printed Antibody Grating,* St. John et al., Analytical Chemistry, vol. 70, No. 6, Mar. 15, 1998, pp. 1108-1111.

Article—*Micro-Scale Patterning of Biological Molecules,* Pritchard et al., Angew. Chem. Int. Ed. Engl., vol. 34, No. 1, 1995, pp. 91-93.

Article—*Oxidation of Self-Assembled Monolayers by UV Light with a Wavelength of 254 nm,* Brewer et al., J. Am. Chem. Soc., vol. 123, 2001, pp. 4089-4090.

Product Data—*Fluorescent Microsphere Standards for Flow Cytometry and Fluorescence Microscopy* from Molecular Probes, Inc. (Invitrogen), 2000, 8 pages.

Article—*Fabrication of Patterned Electrically Conducting Polypyrrole Using a Self-Assembled Monolayer: A Route to All-Organic Circuits,* Gorman, et al., Chem. Mater., vol. 7, 1995, pp. 526-529.

Technical Data Sheet 438, Polysciences, Inc., *Magnetic Microparticles,* Warrington, Pennsylvania, Nov. 2001, 2 pages.

Article—*Microcontact Printing of Octadecylsiloxane on the Surface of Silicon Dioxide and Its Application in Microfabrication,* Xia et al., Journal of the American Chemical Society, vol. 117, Sep. 20, 1995, pp. 9576-9577.

Article-13 *Molecular Design of Temperature-Responsive Polymers as Intelligent Materials,* Okano, Adv. Polym. Sci., vol. 110, 1993, pp. 179-197.

Article—*Patterning self-assembled monolayers using microcontact printing: a new technology for biosensors?,* Mrksich et al., Tibtech, vol. 13, No. 6, Jun. 1995, pp. 228-235.

Article—*Photopatterning and Selective Electroless Metallization of Surface Attached Ligands,* Dressick, et al., Chemistry of Materials, vol. 5, No. 2, 1993, pp. 148-150.

\* cited by examiner

DIFFRACTION-BASED DIAGNOSTIC DEVICES

TECHNICAL FIELD OF THE INVENTION

The present invention relates generally to the field of detecting analytes in a medium, and more particularly to a process for preparing analyte-specific diffraction based diagnostic sensors to indicate the presence of the analyte in a medium.

BACKGROUND

There are many systems and devices available for detecting a wide variety of analytes in various media. Many of the prior systems and devices are, however, relatively expensive and require a trained technician to perform the test. A need has been recognized in the art for biosensor systems that are easy and inexpensive to manufacture, and capable of reliable and sensitive detection of analytes. Reference is made, for example, to U.S. Pat. Nos. 5,922,550; 6,060,256; and 6,221,579 B1.

Various advances have been made in the industry for producing biosensors. For example, U.S. Pat. No. 5,512,131 to Kumar, et al., describes a device that includes a polymer substrate having a metal coating. An analyte specific receptor layer is stamped onto the coated substrate. A diffraction pattern is generated when an analyte binds to the device. A visualization device, such as a spectrometer, is then used to determine the presence of the diffraction pattern. A drawback to this type of device is, however, the fact that the diffraction pattern is not discernible by the naked eye and, thus, a complex visualization device is needed to view the diffraction pattern. Also, the device is generally not able to detect smaller analytes that do not produce a noticeable diffraction pattern.

U.S. Pat. No. 5,482,830 to Bogart, et al., describes a device that includes a substrate which has an optically active surface exhibiting a first color in response to light impinging thereon. This first color is defined as a spectral distribution of the emanating light. The substrate also exhibits a second color which is different from the first color. The second color is exhibited in response to the same light when the analyte is present on the surface. The change from one color to another can be measured either by use of an instrument, or by the naked eye. A drawback with the device is, however, the relatively high cost of the device and problems associated with controlling the various layers that are placed on the wafer substrate.

Contact printing techniques have been explored for producing biosensors having a self-assembling monolayer. U.S. Pat. No. 5,922,550 describes a biosensor having a metalized film upon which is printed (contact printed) a specific predetermined pattern of an analyte-specific receptor. The receptor materials are bound to the self-assembling monolayer and are specific for a particular analyte or class of analytes. Attachment of a target analyte that is capable of scattering light to select areas of the metalized plastic film upon which the receptor is printed causes diffraction of transmitted and/or reflected light. A diffraction image is produced that can be easily seen with the eye or, optionally, with a sensing device. U.S. Pat. No. 6,060,256 describes a similar device having a metalized film upon which is printed a specific predetermined pattern of analyte-specific receptor. The '256 patent is not limited to self-assembling monolayers, but teaches that any receptor which can be chemically coupled to a surface can be used. The invention of the '256 patent uses methods of contact printing of patterned monolayers utilizing derivatives of binders for microorganisms. One example of such a derivative is a thiol. The desired binding agent can be thiolated antibodies or antibody fragments, proteins, nucleic acids, sugars, carbohydrates, or any other functionality capable of binding an analyte. The derivatives are chemically bonded to metal surfaces such as metalized polymer films, for example via a thiol.

A potential issue of the contact printing techniques described above for producing diffraction-based biosensors is the possibility of contamination from the print surface (i.e., stamp) during the printing process. Also, there is the possibility of uneven application or inking of the substances due to pressure and contact variations inherent in the process, as well as surface energy variations.

The present invention relates to a biosensor system that is easy and inexpensive to manufacture, is capable of reliable and sensitive detection of analytes, and avoids possible drawbacks of conventional microcontact printing techniques.

SUMMARY OF THE INVENTION

Objects and advantages of the invention will be set forth in part in the following description, or may be obvious from the description, or may be learned through practice of the invention.

The present invention provides a relatively inexpensive yet sensitive biosensor device, a method for producing such biosensor devices, and a method for detecting and quantifying analytes of interest present in a medium.

The biosensor includes a substrate member upon which a pattern of areas of analyte specific receptive material (i.e., biomolecules) has been defined by a negative or positive photo-oxidation masking process. The substrate may be any one of a wide variety of suitable materials, including plastics, metal coated plastics and glass, functionalized plastics and glass, silicon wafers, foils, glass, etc. Desirably, the substrate is flexible, such as a polymeric film, in order to facilitate the manufacturing process.

Self assembled monolayers of thiol-containing molecules on metal, particularly gold, coated substrates form the basis for a variety of biosensors. Reference is made for example to U.S. Pat. No. 5,922,550, the entire disclosure of which is incorporated herein in its entirety for all purposes. The biosensors and masking process according to the present invention are based generally on the principle that, while the metal-sulfur interaction is extremely strong (nearly as strong as a covalent bond), the interaction is susceptible to oxidation, and that the oxidative process can be accelerated using ultraviolet (UV) light. This principle can be exploited to form a patterned monolayer of biomolecules on a substrate by using UV light and a patterned photomask on a metal coated substrate to which is applied a layer of biomolecules, such as antibodies, enzymes, aptamers, or any other functional biomolecule.

In one particular embodiment, a generally uniform blocking monolayer of thiol-containing molecules is first formed on a metalized substrate, for example a gold-coated substrate (i.e., gold-coated polyethylene-terephthalate). The thiol-containing molecules may be, for example, thioglucose, mercaptoethanol, or any alkanethiolate. A mask having any desired pattern of shielded or "protected" areas and exposed areas (transparent or translucent areas) is then placed over the substrate member. The mask and substrate combination are then exposed to UV light for a time sufficient to oxidize the gold-thiol link between the monolayer and gold coating in the areas of the substrate exposed through the mask. The amount of exposure time to the UV light will depend on the polarity and molecular size of the thiol-containing molecules.

The substrate is then exposed (e.g., coated) with a solution of a thiolated biomolecules. The substrate is exposed to the solution for a sufficient length of time for a monolayer of the thiolated biomolecules to form in the photo-oxidized areas of the substrate. The substrate is then washed with water or a buffer to remove the excess thiolated biomolecules from the unoxidized areas of the substrate. The thiolated biomolecules remain attached to the substrate at the photo-oxidized areas.

In a "positive" mask embodiment, the biosensor would essentially be defined at this point with active discrete areas of receptive material specific for a particular analyte of interest (the thiolated biomolecules) defined in a pattern corresponding to the oxidized areas of the substrate. In this case, the thiolated biomolecule would be chosen such that it specifically binds a particular analyte of interest. The unoxidized areas of the substrate containing the initial thiol-containing blocking molecules define inactive non-binding areas of the biosensor.

In a "negative" mask embodiment, the initial thiolated biomolecules would be chosen such that they do not specifically bind the particular analyte of interest. After the excess biomolecules are washed from the unoxidized areas of the substrate, the substrate is exposed again (without the mask) to the UV light source for a period of time sufficient to oxidize the remaining gold-thiol links between the initial blocking layer of thiol-containing molecules and the gold surface. As with the initial UV exposure, the exposure time will vary but should be much less than the time it would take to oxidize the gold-thiol links of the thiolated biomolecules attached at the first oxidized areas.

The device is then exposed to a second solution of thiolated biomolecules (the receptive material) selected specifically for the analyte of interest. The exposure time is sufficient for a monolayer of the receptive material to form on the second oxidized areas. The excess receptive material is then washed from the substrate. Thus, the biosensor includes a pattern of active areas of biomolecules specific for the analyte of interest, and a pattern of blocking or inactive areas of thiolated biomolecules that will not recognize the analyte of interest.

It should be appreciated that the invention is not limited to any particular pattern defined by the mask. Virtually any number and combination of active shapes are possible. In one particular embodiment, the active area pattern is defined by about 10 micron diameter pixels at a spacing of about 5 microns apart over the test surface of the substrate.

Upon subsequent exposure of the biosensor to a medium containing an analyte of interest, the analyte binds to the receptive material in the active areas. The biosensor will then diffract transmitted light in a diffraction pattern corresponding to the active areas. The diffraction pattern may be visible to the naked eye or, optionally, viewed with a sensing device.

In the case where an analyte does not scatter visible light because the analyte is too small or does not have an appreciable refractive index difference compared to the surrounding medium, a diffraction-enhancing element, such as polymer microparticles, may be used. These micorparticles are coated with a binder or receptive material that also specifically binds to the analyte. Upon subsequent coupling of the analyte to both the patterned biomolecules in the receptive material layer as well as the microparticles, a diffraction image is produced which can be easily seen with the eye or, optionally, with a sensing device.

By "diffraction" it is meant the phenomenon, observed when waves are obstructed by obstacles, of the disturbance spreading beyond the limits of the geometrical shadow of the object. The effect is marked when the size of the object is of the same order as the wavelength of the waves. In the present invention, the obstacles are analytes (with or without or attached microparticles) and the waves are light waves.

In another embodiment of the present invention, nutrients for a specific class of microorganisms can be incorporated into the receptive material layer. In this way, very low concentrations of microorganisms can be detected by first contacting the biosensor of the present invention with the nutrients incorporated therein and then incubating the biosensor under conditions appropriate for the growth of the bound microorganism. The microorganism is allowed to grow until there are enough organisms to form a diffraction pattern.

The present invention provides a low-cost, disposable biosensor which can be mass produced. The biosensors of the present invention can be produced as a single test for detecting an analyte or it can be formatted as a multiple test device. The uses for the biosensors of the present invention include, but are not limited to, detection of chemical or biological contamination in garments, such as diapers, the detection of contamination by microorganisms in prepacked foods such as meats, fruit juices or other beverages, and the use of the biosensors of the present invention in health diagnostic applications such as diagnostic kits for the detection of proteins, hormones, antigens, nucleic acids, microorganisms, and blood constituents. It should be appreciated that the present invention is not limited to any particular use or application.

These and other features and advantages of the present invention will become apparent after a review of the following detailed description of the disclosed embodiments.

DETAILED DESCRIPTION

Figure 1:
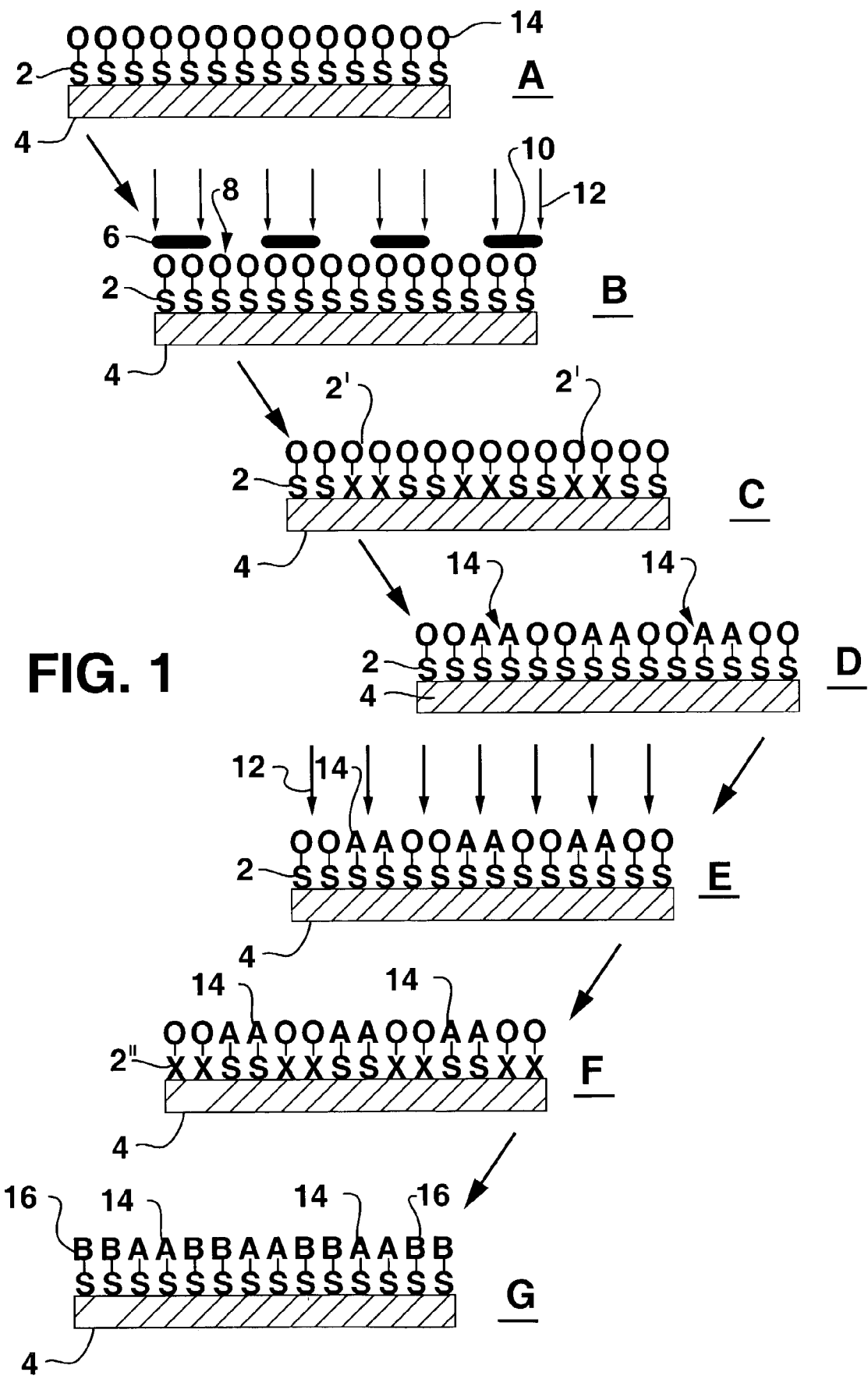
FIG. 1 is a schematic representation of a method for producing biosensors according to the invention by a photo-oxidation masking process.
Figure 2:
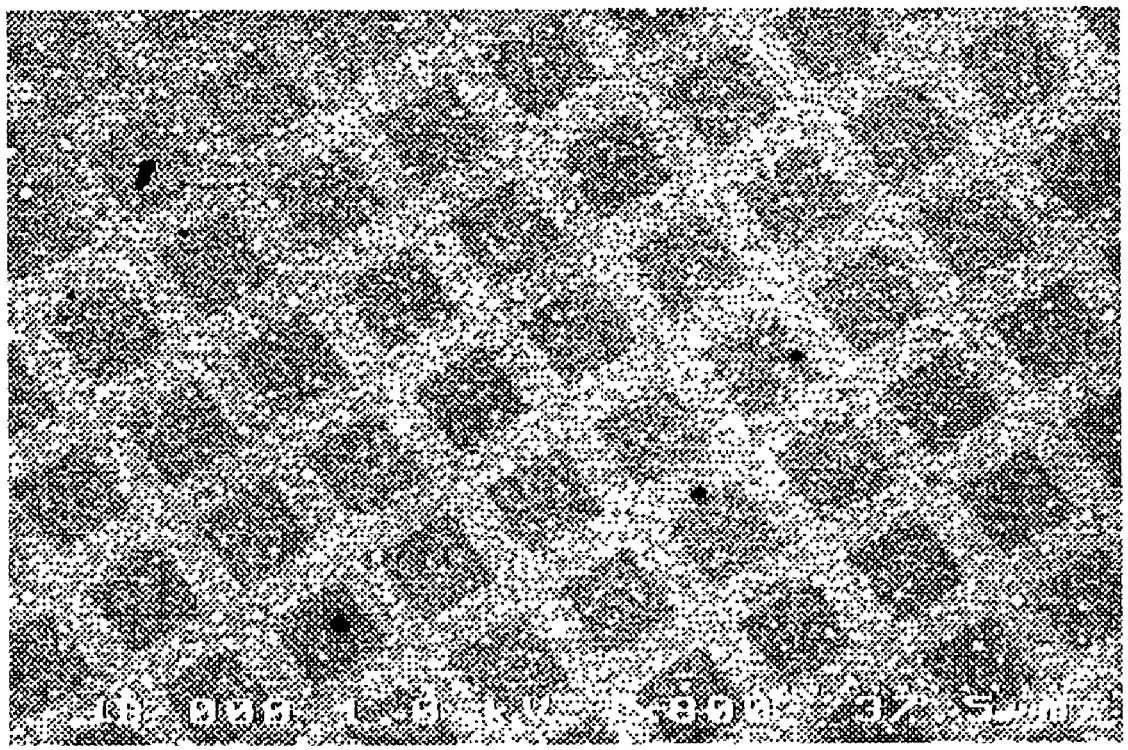
FIG. 2 is a phase-contrast image of active anti-C-reactive protein antibodies in a grid pattern of 10 micron squares spaced 15 microns apart (center-to-center) in a biosensor according to the invention.

The invention will now be described in detail with reference to particular embodiments thereof. The embodiments are provided by way of explanation of the invention, and not meant as a limitation of the invention. For example, features described or illustrated as part of one embodiment may be used with another embodiment to yield still a further embodiment. It is intended that the present invention include these and other modifications and variations as come within the scope and spirit of the invention.

The present invention features improved biosensing devices, and methods for using such biosensing devices, for detecting and quantifying the presence or amount of an analyte of interest within a medium. The analytes that can be detected by the present invention include, but are not limited to, microorganisms such as bacteria, yeasts, fungi, proteins, small molecules, nucleic acids, and viruses. The biosensing devices according to the invention are relatively inexpensive and have advantages over conventional microcontact printed biosensors.

The present invention comprises, in broad terms, a process of defining an active pattern of analyte-specific receptor material on a substrate surface by way of a photo-oxidation masking process. The active areas may be defined in a "negative" or "positive" masking process.

A self-assembled blocking monolayer of thiol-containing molecules is formed on a metal-coated substrate (e.g., gold-coated polyethylene-terephthalate). The thiol-containing molecules may be, for example, thioglucose, mercaptoethanol, or any alkanethiolate. Although there are many different systems of self-assembling monolayers based on different organic components and supports, desired systems for purposes of the present invention are those of alkanethiolates, $HS(CH_2)_nR$, or thiolated saccharides (e.g., thioglucose) on gold films. Typically, a gold film of 5 to 2000 nanometers thick is supported on a titanium-primed Si/Sio2 wafer or glass sheet. Alternatively, a gold-coated (typically coated by plasma deposition) MYLAR® (polyethylene-terephthalate) film may be used. The alkanethiols chemisorb on the gold surface from a solution in which the gold film is immersed, and form adsorbed alkanethiolates with loss of hydrogen. Adsorption can also occur from the vapor. The solution may also be applied by spraying, dipping, coating, spin coating, or any other suitable process for forming a generally uniform layer of the alkanethiolates. Self-assembling monolayers formed on gold from long-chain alkanethiolates of structure $X(CH_2)_nY(CH_2)_mS$ are highly ordered and can be considered as crystalline or quasi-crystaline molecular arrays.

A particularly well suited metal for deposition on the substrate is gold. However, any metal that interacts with sulfur to form a sulfur-metal bond is within the scope of the invention. For example, suitable metals may include silver, aluminum chromium, copper, iron, zirconium, platinum, and nickel.

Any one of a wide variety of materials may serve as the substrate to which the receptive material and blocking material are applied. Such materials are well known to those skilled in the art. For example, the substrate may be formed of any one of a number of suitable plastics, metal coated plastics and glass, functionalized plastics and glass, silicon wafers, glass, foils, etc. Rather than requiring a rigid substrate for the photopatterning process described herein, it has been found that thermoplastic films are quite suitable. Such films include, but are not limited to, polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene—vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80 percent. Other suitable thermoplastics and suppliers may be found, for example, in reference works such as the Modern Plastics Encyclopedia (McGraw-Hill Publishing Co., New York 1923-1996).

The film with metal coating thereon may have an optical transparency of between approximately 5 percent and 95 percent. A more desired optical transparency for the thermoplastic film used in the present invention is between approximately 20 percent and 80 percent. In a desired embodiment of the present invention, the thermoplastic film has at least an approximately 80 percent optical transparency, and the thickness of the metal coating is such as to maintain an optical transparency greater than about 20 percent, so that diffraction patterns can be produced by either reflected or transmitted light. This corresponds to a metal coating thickness of about 20 nanometers. However, in other embodiments of the invention, the metal thickness may be between approximately 1 nanometer and 1000 nanometers.

A mask having any desired pattern of exposed and protected regions is then placed over the substrate and the mask and substrate combination is irradiated with UV light. The mask may be formed of any suitable material that protects or blocks portions of the underlying substrate from the UV light source. A material that has proven useful in the photo-oxidation masking process on a gold-coated MYLAR® film coated with the blocking layer is a transparent or translucent polymer film (such as MYLAR®) having a pattern of shielded or protected regions printed thereon. This type of mask is useful for light sources with a wavelength equal to or greater than about 330 nanometers. For light sources having a wavelength below about 330 nanometers, a quartz or fused silica mask having chrome plated shielded regions defined thereon may be used. The mask may define any pattern of oxidized and unoxidized regions of the blocking layer. The respective regions creating the visible diffraction pattern may be of virtually any size, shape, and pattern. It may be desired to select a size and pattern so as to maximize the visible diffraction contrast between the active and inactive regions. As one example, it has been found suitable if the active regions are defined as generally circular with a diameter of about 10 microns and spaced from each other by about 5 microns.

The time of exposure to the UV light required for oxidizing the exposed areas of the blocking layer will depend on the size and polarity of the thiol-containing molecules. "Small" molecules less than about 500 molecular weight (MW) and more polar molecules are desired in that the oxidizing reaction is more rapid with such molecules. The UV light causes rapid oxidation of the sulfur in the thiol-containing blocking layer and, thus, degradation of the metal-thiol bond at the oxidized sites.

After exposure to the UV light and removal of the mask, a pattern of oxidized areas is defined. These areas will become either active areas of receptive material (positive masking) or shielded inactive areas (negative masking).

The substrate is then exposed to a solution of a thiolated biomolecule. The solution may be applied by any appropriate method, such as dipping, spraying, coating, spin coating, etc. The solution essentially washes away the oxidized molecules (sulfates) such that a bare metal surface is exposed at the oxidized sites. It should be appreciated that an intervening washing step may be carried out for this purpose prior to exposing the substrate to the thiolated biomolecule. The exposure time is sufficient for a monolayer of the thiolated biomolecules to form on the substrate at the oxidized sites. It should be ensured that the concentration of the biomolecule agent in the solution is sufficient to deposit a relatively uniform layer of the material on the substrate. In a "positive" masking process, the biomolecule is selected to be specific for a particular analyte of interest. In other words, the biomolecules recognize the target ligand. In a "negative" masking process, the biomolecule is a blocking agent and is selected specifically not to recognize the analyte of interest.

The thiolated biomolecules thus displace the oxidized blocking molecules and attach to the metal surface with a strong thiol-metal bond. The excess thiolated biomolecules are disassociated from the unoxidized areas of the substrate by washing or rinsing the substrate with water or a buffer solution.

For a positive masking process, the thiolated biomoleclues attached at the ozxidized regions may be specific for the analyte of interest. In this case, localized active areas of receptive material are defined in a pattern corresponding to the oxidized areas and the remaining regions of the substrate with the initial blocking layer define shielded or inactive areas.

For a negative masking process, the substrate is exposed again (without the mask) to the UV light source for a period of time sufficient to oxidize the remaining metal-thiol links between the initial blocking layer of thiol-containing molecules and the metal surface (the second oxidized areas) without oxidizing the metal-thiol links of the thiolated biomolecules attached at the first oxidized areas. The substrate is then exposed to a second solution of thiolated biomolecules selected specifically for the analyte of interest by dipping, rolling, spraying, coating, etc. The solution washes away the oxidized molecules (sulfates) from the second oxidized areas and a monolayer of the second thiolated biomolecules is formed on the substrate at the second oxidized areas, with the biomolecules specifically attaching to the metal surface at the second oxidized areas by a metal-thiol bond. The excess receptive material is then washed from the substrate. Thus, the biosensor includes a pattern of active areas of biomolecules specific for the analyte of interest, and a pattern of blocking or inactive areas of thiolated biomolecules that will not recognize the analyte of interest.

It should be understood that "pattern" includes as few as one active area and one inactive area.

Upon subsequent exposure of the biosensor to a medium containing the analyte of interest, such analyte will bind to the receptors in the active receptive material areas. The analyte results in diffraction of transmitted and/or reflected light in a visible diffraction pattern corresponding to the active areas. As discussed in greater detail below, an enhancer may be used for enhancing diffraction from extremely small analytes.

The analytes that are contemplated as being detected using the present invention include, but are not limited to, bacteria; yeasts; fungi; viruses; rheumatoid factor; antibodies, including, but not limited to IgG, IgM, IgA, IgD, and IgE antibodies; carcinoembryonic antigen; streptococcus Group A antigen; viral antigens; antigens associated with autoimmune disease; allergens; tumor antigens; streptococcus Group B antigen; HIV I or HIV II antigen; or host response (antibodies) to these and other viruses; antigens specific to RSV or host response (antibodies) to-the virus; antigen; enzyme; hormone; polysaccharide; protein; lipid; carbohydrate; drug or nucleic acid; Salmonella species; Candida species, including, but not limited to *Candida albicans* and *Candida tropicalis; Neisseria meningitides* groups A, B, C, Y and W sub 135, *Streptococcus pneumoniae, E. coli, Haemophilus influenza* type A/B; an antigen derived from microorganisms; PSA and CRP antigens; a hapten; a drug of abuse; a therapeutic drug; an environmental agent; and antigens specific to Hepatitis. In broad terms, the "analyte of interest" may be thought of as any agent whose presence or absence from a biological sample is indicative of a particular health state or condition.

It is also contemplated that nutrients for a specific class of microorganism can be incorporated into the receptive material layer. In this way, very low concentrations of microorganisms can be detected by exposing the biosensor of the present invention with the nutrients incorporated therein to the suspect medium and then incubating the biosensor under conditions appropriate for the growth of the bound microorganism. The microorganisms are allowed to grow until there are enough organisms to form a diffraction pattern. Of course, in some cases, the microorganism is present or can multiply enough to form a diffraction pattern without the presence of a nutrient in the active receptive material areas.

The receptive material is characterized by an ability to specifically bind the analyte or analytes of interest. The variety of materials that can be used as receptive material is limited only by the types of material which will combine selectively (with respect to any chosen sample) with a secondary partner. Subclasses of materials which fall in the overall class of receptive materials include toxins, antibodies, antibody fragments, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, aptamers, peptides and any other member of a specific binding pair. This list only incorporates some of the many different materials that can be coated onto the substrate surface to produce a thin film assay system. Whatever the selected analyte of interest is, the receptive material is designed to bind specifically with the analyte of interest.

The matrix or medium containing the analyte of interest may be a liquid, a solid, or a gas, and can include a bodily fluid such as mucous, saliva, urine, fecal material, tissue, marrow, cerebral spinal fluid, serum, plasma, whole blood, sputum, buffered solutions, extracted solutions, semen, vaginal secretions, pericardial, gastric, peritoneal, pleural, or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasm component, pili or flagella component, protein, polysaccharide, drug, or any other material. For example, receptive material for bacteria may specifically bind a surface membrane component, protein or lipid, a polysaccharide, a nucleic acid, or an enzyme. The analyte which is specific to the bacteria may be a polysaccharide, an enzyme, a nucleic acid, a membrane component, or an antibody produced by the host in response to the bacteria. The presence or absence of the analyte may indicate an infectious disease (bacterial or viral), cancer or other metabolic disorder or condition. The presence or absence of the analyte may be an indication of food poisoning or other toxic exposure. The analyte may indicate drug abuse or may monitor levels of therapeutic agents.

One of the most commonly encountered assay protocols for which this technology can be utilized is an immunoassay. However, the general considerations apply to nucleic acid probes, enzyme/substrate, and other ligand/receptor assay formats. For immunoassays, an antibody may serve as the receptive material or it may be the analyte of interest. The receptive material, for example an antibody or an antigen, should form a stable, reactive layer on the substrate surface of the test device. If an antigen is to be detected and an antibody is the receptive material, the antibody must be specific to the antigen of interest; and the antibody (receptive material) must bind the antigen (analyte) with sufficient avidity that the antigen is retained at the test surface. In some cases, the analyte may not simply bind the receptive material, but may cause a detectable modification of the receptive material to occur. This interaction could cause an increase in mass at the test surface, a decrease in the amount of receptive material on the test surface, or a change in refractive index. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptive material occurs is not important to this invention, but may impact the reaction conditions used in the final assay protocol.

In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern becomes discernible in less than one hour after contact of the analyte with the biosensing device of the present invention.

The diffraction grating which produces the diffraction of light upon interaction with the analyte must have a minimum periodicity of about ½ the wavelength and a refractive index different from that of the surrounding medium. Very small analytes, such as viruses or molecules, can be detected indirectly by using a larger, "diffraction-enhancing element," such as a micro-particle, that is specific for the small analyte. One embodiment in which the small analyte can be detected comprises coating the enhancing particle, such as a latex bead or polystyrene bead, with a receptive material, such as an antibody, that specifically binds to the analyte of interest. Particles that can be used in the present invention include, but are not limited to, glass, cellulose, synthetic polymers or plastics, latex, polystyrene, polycarbonate, proteins, bacterial or fungal cells, silica, cellulose acetate, carbon, and the like. The particles are desirably spherical in shape, but the structural and spatial configuration of the particles is not critical to the present invention. For instance, the particles could be slivers, ellipsoids, cubes, random shape and the like. A desirable particle size ranges from a diameter of approximately 0.1 micron to 50 microns, desirably between approximately 0.1 micron and 2.0 microns. The composition of the particle is not critical to the present invention.

Desirably, the receptive material layer on the substrate will specifically bind to an epitope on the analyte that is different from the epitope used in the binding to the enhancing particle. Thus, for detecting a small analyte in a medium, the medium is first exposed to the latex particles having the virus-specific receptive material thereon. The small analytes of interest in the medium will bind to the latex particles. Then, the latex particles are optionally washed and exposed to the biosensor film with the pattern of active receptive material areas containing the virus-specific antibodies. The antibodies then bind to the viral particles on the latex bead thereby immobilizing the latex beads in the same pattern as the active areas on the film. Because the bound latex beads will cause diffraction of the visible light, a diffraction pattern is formed, indicating the presence of the viral particle in the liquid. Other combinations using diffraction enhancing particles are described, for example, in U.S. Pat. No. 6,221,579 incorporated herein for all purposes.

The first and second thiolated biomolecule solutions may be applied to the substrate by any conventional method. The material is applied so that it generally uniformly covers an entire (for example, upper) surface of the substrate. Non-contact methods for applying the receptive material may be desired so as to eliminate the possibility of contamination by contact during application. Suitable application methods include, but are not limited to, dipping, spraying, rolling, spin coating, and any other technique wherein the solutions can be applied generally uniformly over the entire test surface of the substrate.

The technique selected should minimize the amount of biomolecule solution required for coating a large number of test surfaces and maintain the stability/functionality of the receptive material during application. The technique should also apply or adhere the receptive material to the substrate in a uniform and reproducible fashion.

FIG. 1 is a schematic representation of one method for producing biosensors by a photo-oxidation method according to the invention. Step A represents a thiol-containing blocking layer 2 applied to a substrate member 4. Step B represents a mask 6 disposed over the substrate member 4. The mask 6 includes exposed or open regions 8 and shielded or protected regions 10 defined thereon. The mask 6 and substrate 4 combination are exposed to a UV light 12. The areas of the substrate 4 under the protected regions 10 of the mask 6 are protected from the light 12, and the areas of the blocking layer 2 under the open areas 8 of the mask 6 are exposed to the light 12. Step C represents the device after exposure to the light 12 and removal of the mask 6. The blocking layer material 2' exposed to the light 12 has been oxidized such that a pattern of oxidized areas are defined on the substrate member 4. Step D represents the device after it has been exposed to a first thiolated biomolecule solution. The oxidized particles 2' have been displaced by a monolayer of the thiolated biomolecules 14. For a positive masking procedure, the biomolecules 14 are specific for the analyte of interest and the biosensor is essentially defined at this point. For a negative masking procedure, the biomolecules 14 are a blocking agent and the further steps are taken to define the active areas of receptive material. Step E-represents the device being exposed a second time to the UV light 12 without the mask 6. The exposure time is sufficient to oxidize the remaining areas of the initial blocking layer material 2 without disrupting the gold-thiol bond between the substrate member 4 and biomolecules 14. Step F represents the device after the second exposure. The remaining blocking layer material 2 is oxidized (represented by 2") and the areas of biomolecules 14 remain intact. Step G represents the device after it has been exposed to a second solution of thiolated biomolecules. The oxidized particles 2" have been displaced by the second thiolated biomolecules 16 that are specific for the analyte of interest. At this point, the biosensor is defined by a pattern of active receptive material areas (areas of biomolecule 16) and a pattern of inactive or shielded areas (areas of blocking biomolecule 14).

The biosensors according to the invention have a wide range of uses in any number of fields. The uses for the biosensors of the present invention include, but are not limited to, detection of chemical or biological contamination in garments, such as diapers, generally the detection of contamination by microorganisms in prepacked foods such as meats, fruit juices or other beverages, and the use of the biosensors of the present invention in health diagnostic applications such as diagnostic kits for the detection of proteins, hormones, antigens, DNA, microorganisms, and blood constituents. The present invention can also be used on contact lenses, eyeglasses, window panes, pharmaceutical vials, solvent containers, water bottles, band-aids, wipes, and the like to detect contamination. In one embodiment, the present invention is contemplated in a dipstick form in which the patterned substrate is mounted at the end of the dipstick. In use the dipstick is dipped into the liquid in which the suspected analyte may be present and allowed to remain for several minutes. The dipstick is then removed and then, either a light is projected through the substrate or the substrate is observed with a light reflected from the substrate. If a diffraction pattern is observed, then the analyte is present in the liquid.

In another embodiment of the present invention, a multiple analyte test is constructed on the same support. A strip may be provided with several patterned substrate sections. Each section has a different receptive material that is different for different analytes. It can be seen that the present invention can be formatted in any array with a variety of patterned substrates thereby allowing the user of the biosensor device of the present invention to detect the presence of multiple analytes in a medium using a single test.

In yet another embodiment of the present invention, the biosensor can be attached to an adhesively backed sticker or decal which can then be placed on a hard surface or container wall. The biosensor can be placed on the inside surface of a container such as a food package or a glass vial. The biosensor can then be visualized to determine whether there is microbial contamination.

The invention is further illustrated by the following example, which are not to be construed in any way as imposing limitations upon the scope of the invention. It should be understood that resort may be had to various other embodiments, modifications, and equivalents thereof, which, after reading the description of the invention herein, may suggest themselves to those skilled in the art without departing from the scope and spirit of the present invention.

EXAMPLE 1

Gold-coated mylar (gold thickness~10 nanometer, <20 ohms resistance, total thickness of 3-7 mils, from Courtaulds Performance Films, Canoga Park, Calif.) was exposed to a 100 mM solution of thio-b-1-D-glucose for 5 min followed by a rinse with water. The film was blown dry and then mounted in a vacuum frame in intimate contact with a photomask. The chrome-on-quartz photomask was produced by direct-write e-beam with a pattern that was a regular grid of 10 um diameter squares spaced 15 um center-to-center (positive image). The film was exposed to broadband UV light using a solar simulator without filters (LS-1000, Solar Light, Philadelphia, Pa.) for 10 min. The film was removed from the vacuum frame and exposed for 10 min to a 1 mg/ml solution of thiolated anti-lutenizing hormone beta subunit (LH) monoclonal antibody (Fitzgerald, #10-115, lot#191) The antibody was thiolated using Sulfo-LC-SPDP (Pierce cat # 21650ZZ) and purified using gel-filtration. After exposure to the anti-LH antibody the film was exposed for an additional 10 min to broadband UV light using the solar simulator, however without a photomask. The film was then dipped in a 1 mg/ml solution of thiolated anti-C-reactive protein (CRP) monoclonal antibody (Biospacific, #A58040136P, lot# A0640) for 10 min. The anti-CRP antibody was thiolated in the same manner as the anti-LH antibody. After exposure to the anti-CRP antibody, the film was washed with filtered water and blown dry with filtered air.

The resulting pattern of anti-CRP antibody zones was visualized using an enzyme-based assay that generates a colored precipitate. A 1 ug/mL solution of C-reactive protein that was covalently linked to horseradish peroxidase (Dako, #P0227, lot#074-301) was reacted with the patterned antibody surface for 10 min followed by a rinse with PBS (50 mM, pH 7.4 phosphate buffer, 150 mM sodium chloride). The slide was then blown dry with filtered air. The residual horseradish peroxidase (localized to the active zones via antibody recognition of the C-reactive protein) was visualized by precipitation of tetramethyl benzidine (KPL Microwell peroxidase substrate, #50-76-04 and KPL Membrane Enhancer, #50-77-01).

What is claimed is:

1. A method for producing biosensors, comprising:
    forming a blocking layer of thiol-containing molecules on a metalized substrate member, the thiol-containing molecules forming thiol-metal bonds with the metal surface of the substrate member;
    exposing the substrate member to an oxidizing enhancing stimulus through a mask having a pattern of exposed areas and protected areas, said exposure being of sufficient time to oxidize the thiol-metal bonds in the exposed areas of the blocking layer under the mask;
    exposing the substrate member to a first source of thiolated biomolecules without an intervening washing step, for a time sufficient to remove the oxidized thiol-metal bonds in the exposed areas and form a layer of the first thiolated biomolecules directly on the metalized substrate member at the oxidized areas of the blocking layer by displacing the oxidized thiol-containing molecules in the exposed areas with the first thiolated biomolecule, the first thiolated biomolecules being specific for an analyte of interest having a particular size, the first thiolated biomolecules defining active areas of receptive material in a pattern corresponding to the oxidized areas defined by the exposing to oxidize step, wherein when the biosensor is exposed to a medium containing the analyte of interest, the analyte binds to the receptive material in the active areas such that the particular size of the analyte of interest, with or without a diffraction enhancing element, facilitates subsequent diffraction of light in a diffraction pattern corresponding to the active areas.

2. The method as in claim 1, wherein the first thiolated biomolecules are selected from at least one of antigens, antibodies, nucleotides, chelators, enzymes, bacteria, yeasts, fungi, viruses, bacterial pili, bacterial flagellar materials, nucleic acids, polysaccharides, lipids, proteins, carbohydrates, metals, hormones, and respective receptors for said materials.

3. The method as in claim 1, wherein the oxidizing enhancing stimulus is a UV light source.

4. The method as in claim 1, wherein the metalized substrate is gold-coated.

5. The method as in claim 1, comprising selecting the substrate member from the group of materials consisting of plastics, metal coated plastics and glass, functionalized plastics and glass, silicon wafers, and foils.

6. The method as in claim 1, wherein the substrate member comprises a polymer film coated with a metal.

7. The method as in claim 6, wherein the polymer film comprises polyethylene-terephthalate.

8. The method as in claim 6, comprising selecting the metal from the group consisting of gold, silver, chromium, nickel, platinum, aluminum, iron, copper, gold oxide, chromium oxide and zirconium.

9. The method as in claim 1, comprising viewing a diffraction pattern of active areas with a naked eye.

10. The method as in claim 1, wherein the analyte of interest is selected from at least one of a bacteria, yeast, fungus, virus, rheumatoid factor, IgG, IgM, IgA, IgD and IgE antibodies, carcinoembryonic antigen, streptococcus Group A antigen, viral antigens, antigens associated with autoimmune disease, allergens, tumor antigens, streptococcus group B antigen, IIV I or HIV II antigen, antibodies viruses, antigens specific to RSV, an antibody, antigen, enzyme, hormone, polysaccharide, protein, lipid, carbohydrate, drug, nucleic acid, Neisseria meningitides groups A, B, C, Y and W sub 135, Streptococcus pneumoniae, E. coli K1, Haemophllus influenza type A/B, an antigen derived from microorganisms, PSA and CRP antigens, a hapten, a drug of abuse, a therapeutic drug, an environmental agents, or antigens specific to Hepatitis.

11. The method as in claim 1, wherein the first thiolated biomolecules are non-specific for a particular analyte of interest, and further comprising exposing the substrate member a second time to the oxidizing stimulus without the mask for a sufficient time to oxidize the thiol-metal bonds in the remaining areas of the blocking layer, and subsequently exposing the substrate member to a second source of thiolated biomolecules that are specific for the analyte of interest for a time sufficient for a layer of the second thiolated biomolecules to form at the second oxidized areas, the areas containing the second thiolated biomolecules defining active areas of receptive material, and the areas containing the first thiolated biomolecules defining shielded areas of the substrate, and wherein when the biosensor is exposed to a medium containing the analyte of interest, the analyte binds to the receptive material in the active areas and facilitate subsequent diffraction of transmitted light in a diffraction pattern corresponding to the active areas.

12. The method as in claim 11, wherein the second thiolated biomolecules are selected from at least one of antigens, antibodies, nucleotides, chelators, enzymes, bacteria, yeasts, fungi, viruses, bacterial pili, bacterial flagellar materials, nucleic acids, polysaccharides, lipids, proteins, carbohydrates, metals, hormones, and respective receptors for said materials.

13. The method as in claim 11, wherein the analyte of interest is selected from at least one of a bacteria, yeast, fungus, virus, rheumatoid factor, IgG, IgM, IgA, IgD and IgE antibodies, carcinoembryonic antigen, streptococcus Group A antigen, viral antigens, antigens associated with autoimmune disease, allergens, tumor antigens, streptococcus group B antigen, IIV I or HIV II antigen, antibodies viruses, antigens specific to RSV, an antibody, antigen, enzyme, hormone, polysaccharide, protein, lipid, carbohydrate, drug, nucleic acid, *Neisseria meningitides* groups A, B, C, Y and W sub 135, *Streptococcus pneumoniae, E. coil* K1, *Haemophllus influenza* type A/B, an antigen derived from microorganisms, PSA and CRP antigens, a hapten, a drug of abuse, a therapeutic drug, an environmental agents, or antigens specific to Hepatitis.

14. The method as in claim 11, wherein the oxidizing enhancing stimulus is a UV light source.

15. The method as in claim 11, wherein the metalized substrate is gold-coated.

16. The method as in claim 11, comprising selecting the substrate member from the group of materials consisting of plastics, metal coated plastics and glass, functionalized plastics and glass, silicon wafers, and foils.

17. The method as in claim 11, wherein the substrate member comprises a polymer film coated with a metal.

18. The method as in claim 17, wherein the polymer film comprises polyethylene-terephthalate.

19. The method as in claim 1, wherein the thiol-containing molecules consist essentially of thioglucose.

* * * * *